(12) United States Patent
Bordet et al.

(10) Patent No.: US 8,354,395 B2
(45) Date of Patent: Jan. 15, 2013

(54) METHOD FOR PROVIDING NEUROPROTECTION FROM SPINAL MUSCULAR ATROPHY

(75) Inventors: Thierry Bordet, Marseilles (FR); Cyrille Drouot, Marseilles (FR); Bruno Buisson, Marseilles (FR)

(73) Assignee: Trophos, Marseille Cedex (FR)

( * ) Notice: Subject to any disclaimer, the term of this patent is extended or adjusted under 35 U.S.C. 154(b) by 0 days.

(21) Appl. No.: 13/591,789

(22) Filed: Aug. 22, 2012

(65) Prior Publication Data

US 2012/0316141 A1 Dec. 13, 2012

Related U.S. Application Data

(62) Division of application No. 12/776,217, filed on May 7, 2010, now Pat. No. 8,283,341, which is a division of application No. 10/548,473, filed as application No. PCT/FR2004/000532 on Mar. 5, 2004, now Pat. No. 7,858,603.

(30) Foreign Application Priority Data

Mar. 11, 2003 (FR) .................................. 03 02992
Sep. 26, 2003 (FR) .................................. 03 11324

(51) Int. Cl.
*A61K 31/375* (2006.01)
*C07J 9/00* (2006.01)
*C07J 41/00* (2006.01)

(52) U.S. Cl. ..................................................... 514/169
(58) Field of Classification Search .................. 514/169; 552/520, 540

See application file for complete search history.

(56) References Cited

PUBLICATIONS

Ponsold, K. et al., "Nitrogen-containing steroids V. Epimeric 3-acetamido-4-cholestenes", Journal Fuer Praktische Chemie, (1964), vol. 23, No. 3-4, pp. 173-176, XP-008020603.
Uenseren, E., "Gamma irradiation of cholestenone oximes", Report, (1976), vol. 8, No. 6, 21 pages, XP-00164118.
Suginome, H. et al., "Photo-induced Molecular Transformations. Part 87. Regiospecific Photo-Beckmann Rearrangement of Steroidal α,β-Unsaturated Ketone Oximes: Synthesis of Some Steroidal Enamino Lactams", J. Chem Soc., (1988), pp. 321-326, XP-002277500.
Dorszewska, J. et al., "Patterns of free and sterified sterol fractions of the cerebral white matter in severe and moderate experimental hypoxia", Medical Science Monitor, (2000), vol. 6, No. 2, pp. 227-231, abstract only, XP-002277501.
Evans et al., "Effect of molecular environmental on the absorption spectra of organic compounds in solution. III. Compounds containing the chromophore C:C|C|:N", J. Chem. Soc., pp. 565-571, 1943.
Evans et al., "Effect of molecular environment of the absorption spectra of organic compounds in solution. III. Compounds containing the chromophore C:C|C|:N", J. Chem. Soc., pp. 565-571, 1943 (Abstract).
Hutchins et al., "Stereoselective hydride reductions of cyclic alpha, beta-unsaturated N-diphenylphosphinyl imines to protected allylic amines.", J. Org. Chem., vol. 63, pp. 8077-0808, 1998.

*Primary Examiner* — San-Ming Hui
*Assistant Examiner* — Kathrien Cruz
(74) *Attorney, Agent, or Firm* — Browdy and Neimark, PLLC

(57) ABSTRACT

A method for providing neuroprotection to a patient in need of neuroprotection, comprising administering a neuroprotective-effective amount of a compound of formula I

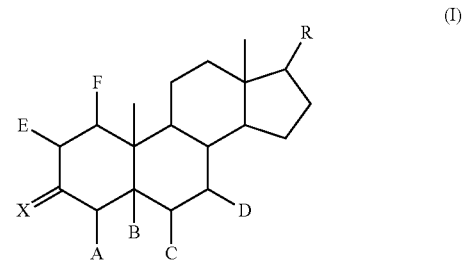

(I)

in which X is an oxygen atom or an =N—OH group,
R is selected from the group consisting of

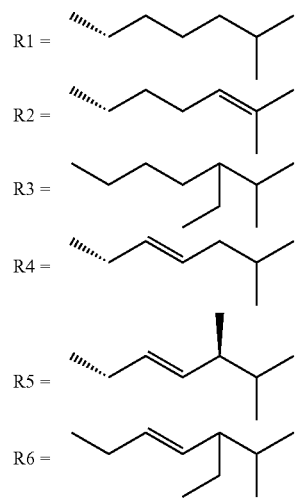

A is a hydrogen atom or together with B a carbon-carbon bond,
B is a hydrogen atom, a hydroxy group or together with A a carbon-carbon bond,
C is a hydrogen atom or together with D a carbon-carbon bond,
D is a hydrogen atom or together with C a carbon-carbon bond,
E is a hydrogen atom or together with F a carbon-carbon bond,
F is a hydrogen atom or together with E a carbon-carbon bond,
or an addition salt with a pharmaceutically acceptable acid.

2 Claims, No Drawings

METHOD FOR PROVIDING NEUROPROTECTION FROM SPINAL MUSCULAR ATROPHY

The present invention relates to the use as medicaments of derivatives of cholest-4-en-3-one, in particular as neuroprotectors for example in the pathologies and the traumatisms linked to the degeneration or death of the motor neurons, the pharmaceutical compositions containing them, novel derivatives and their preparation process.

Neurodegenerative processes are characterized by the dysfunction and death of the neurons leading to the loss of the neurological functions mediated by the brain (central nervous system, CNS), the spinal cord and the peripheral nervous system (PNS). They can result, amongst others, from pathological situations known collectively under the term of neurodegenerative diseases or affections, traumatism, or exposure to toxins.

The most important pathologies which are characterized by a degenerative process are:
- the hereditary or sporadic, chronic neurodegenerative diseases, in particular Alzheimer's disease, Huntington's chorea, Parkinson's disease, amyotrophic lateral sclerosis, spinal amyotrophies, Creutzfeldt-Jakob's disease, multiple sclerosis, adrenoleukodystrophy, epilepsy, dementia, schizophrenia, and the neurological syndromes associated with AIDS;
- neuronal lesions linked with ageing;
- the hereditary peripheral neuropathies or peripheral neuropathies resulting from a lesion, such as Fabry's disease, Charcot-Marie-Tooth disease, Krabbe's disease, leukodystrophies, diabetic neuropathies and those induced by anti-cancer treatments;
- traumatisms of the brain, the peripheral nerves or the spinal cord;
- ischemias of the brain or the spinal cord following a cerebro-vascular accident, or induced by a lack of blood irrigation;
- degenerations which are hereditary, traumatic or linked with ageing of the sensory neurons of vision, such as the macular degenerations, pigmentary retinitis, or degenerations of the optic nerve induced by glaucomas;
- degenerations which are hereditary, resulting from a lesion or linked with ageing of the sensory neurons of hearing leading to a reduction or a loss of audition.

A part of the signalling pathways affected in these pathologies are common to a large number of neurodegenerative diseases. Alzheimer's disease is the most frequent dementia. It causes the appearance of atrophy of the brain, a predominant neuronal loss in the hippocampus and it also affects the cholinergic neurons. Other pathologies, such as the lobar atrophies (Pick's disease, Creutzfeld-Jakob's disease), Lewy body dementia, vascular dementias, Parkinson's disease are associated with significant neuronal death at the outset of the symptoms of these dementias.

Currently an effective treatment does not exist to check the neuronal degenerations. A therapeutic approach for protecting the neurons from dying is the supply of neurotrophic proteins.

These proteins, such BDNF (brain-derived neurotrophic factor), CNTF (ciliary neurotrophic factor), NGF (nerve growth factor), GDNF (glia-derived neurotrophic factor) are synthesized during embryonal development or after lesion in adults. These growth factors encourage the survival, matura tion and differentiation of neuronal cells. Moreover, they inhibit the apoptotic mechanisms, activate multiple survival pathways and protect a large number of neuronal populations. Their use is proposed in the majority of the neuronal degenerations.

Compounds which would activate the expression of neurotrophic factors or which would mimic the action of these factors have a therapeutic potential for the treatment of neurodegenerative syndromes.

In particular, the supply of neurotrophic molecules for the treatment of neuronal degenerations has three objectives:
- to compensate for a potential deficiency in neurotrophic factors linked to a failure of supply by the peripheral or central targets of the neurons and/or a problem with the retrograde transport of these factors;
- to intervene in a non-specific fashion on the biochemical pathways involved in the degenerative cascade;
- to encourage the natural compensator phenomena of dendritic growth and arborization of the nerve endings.

These compounds would therefore have a beneficial effect in a large number of pathologies in particular in the pathologies affecting the peripheral and central nervous systems.

Moreover, within the above context, the motor neurons are neurons in particular present in the spinal cord and the brain stem. Their degeneration or their death can lead to a progressive weakening of the muscles of the limbs, then to atrophy and possibly to spasticity (i.e. a permanent contraction) of the muscle.

The most important pathologies which result from the degeneration and death of the spinal and/or bulbar motor neurons are amyotrophic lateral sclerosis, also known under the name of Charcot's disease or also Lou Gehrig's disease, and infantile spinal amyotrophies, also known under the names of Werdnig-Hoffmann disease or Kugelberg-Welander disease.

Moreover, a degeneration of the motor neurons is observed in the case of traumas with crushing and/or severing of the spinal cord or the peripheral motor nerves.

More generally, spinal amyotrophies are referred to as diseases where the degeneration or death of the motor neurons of the spinal cord are involved.

Amyotrophic lateral sclerosis (ALS) is a neurodegenerative disease associated with different types of inclusions such as Lewy bodies and characterized by a degeneration of the spinal and cortical motor neurons the fatal outcome of which is sometimes associated with frontal dementia. During the development of ALS, the degenerative phenomena occur not only in the brain but also in the spinal cord and consequently in the muscle, by lack of innervation.

Active compounds for combating the diseases mentioned above are always being sought.

Now the Applicant has discovered that the derivatives of 4-cholesten-3-one and in particular cholest-4-en-3-one oxime are endowed with remarkable neuroprotective properties, particularly vis à vis the motor neurons, the neurons of the central nervous system, of the motor and peripheral nerves, and therefore are of use as medicaments, and that certain of them are moreover endowed with remarkable properties for inhibiting the effect of positive allosteric modulators of the $GABA_A$ (gamma amino butyric acid of type A) receptors.

This is why a subject of the present invention is the compounds corresponding to the formula I

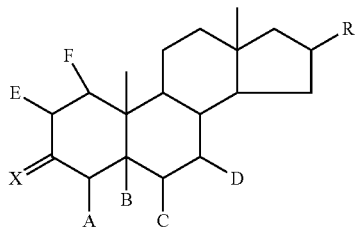

(I)

in which X represents an oxygen atom or an =N—OH group,
R represents a group chosen from

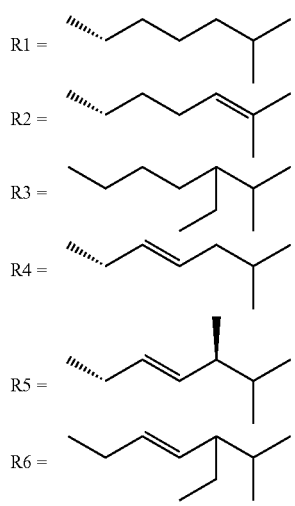

A represents a hydrogen atom or together with B a carbon-carbon bond,
B represents a hydrogen atom, a hydroxy group or together with A a carbon-carbon bond,
C represents a hydrogen atom or together with D a carbon-carbon bond,
D represents a hydrogen atom or together with C a carbon-carbon bond,
E represents a hydrogen atom or together with F a carbon-carbon bond,
F represents a hydrogen atom or together with E a carbon-carbon bond,
as well as their addition salts with pharmaceutically acceptable acids, with the exception of cholest-4-en-3-one, 24-ethylcholest-4,22-dien-3-one, 5-beta-cholestan-3-one and cholest-4,6-dien-3-one as well as cholest-4,24-dien-3-one, 24-methylcholest-4,6,22-trien-3-one, and cholest-5-en-3-one oxime, for their use in a therapeutic treatment method for the human or animal body, i.e. as medicaments.

The addition salts with pharmaceutically acceptable acids can be for example the salts formed with the following acids: hydrochloric, hydrobromic, nitric, sulphuric, phosphoric acetic, formic, propionic, benzoic, maleic, fumaric, succinic, tartaric, citric, oxalic, glyoxylic, aspartic, alkane sulphonic such as methane or ethane sulphonic acids, arylsulphonic, such as benzene or paratoluene sulphonic acids, or carboxylic acid.

Among the compounds described above, the compounds of formula I for which X represents an =N—OH group as well as their addition salts with pharmaceutically acceptable acids are in particular retained.

More particularly the above compounds are retained for which,

X represents an =N—OH group, A represents together with B a carbon-carbon bond, C, D, represent a hydrogen atom, E, F represent a hydrogen atom or together a carbon-carbon bond and R has the meaning R1, X represents an =N—OH group, A represents together with B a carbon-carbon bond, C, D represent a hydrogen atom, E, F represent a hydrogen atom and R has the meaning R2 or R3 or R4, X represents an =N—OH group, A represents together with B a double bond, C represents together with D a carbon-carbon bond, E, F represent a hydrogen atom and R has the meaning R1 or R6, X represents an =N—OH group, A represents together with B a double bond, C represents together with D a carbon-carbon bond, E represents together with F a carbon-carbon bond represent a hydrogen atom and R has the meaning R1

X represents an =N—OH group, E represents together with F a double bond, C, D, A, B represent a hydrogen atom and R has the meaning R1, as well as their addition salts with pharmaceutically acceptable acids Among the compounds of the invention there can moreover be mentioned
5β-hydroxy-cholest-4-en-3-one
cholestan-3-one oxime
as well as their addition salts with the pharmaceutically acceptable acids.

Quite particularly the following are retained:
cholest-4-en-3-one oxime,
1,4-cholestadien-3-one oxime
as well as their addition salts with the pharmaceutically acceptable acids.

The compounds which are a subject of the present invention have very useful pharmacological properties. They are endowed in particular with remarkable neuroprotective properties, particularly vis à vis the motor neurons.

These properties are illustrated hereafter in the experimental part. They justify the use of the compounds described above as well as their addition salts with the pharmaceutically acceptable acids as a medicament.

The medicaments according to the present invention are of use due to their neuroprotectrive properties for example in the treatment or the prevention of the neurodegenerative diseases, such as for example Huntington's disease, hereditary or sporadic, chronic neurodegenerative diseases, neuronal lesions linked with ageing, hereditary peripheral neuropathies or peripheral neuropathies resulting from a lesion, Charcot-Marie-Tooth disease, diabetic neuropathies or neuropathies induced by anti-cancer treatments, traumas of the brain, of the peripheral nerves or of the spinal cord, ischemias of the brain or the spinal cord, degenerations which are hereditary, resulting from a lesion or linked with ageing of the sensory neurons of vision or degenerations of the optic nerve, degenerations which are hereditary, traumatic or linked with ageing of the sensory neurons of hearing, lobar atrophies and vascular dementias, and in particular spinal amyotrophies, amyotrophic lateral sclerosis and pathologies due to traumas of the spinal cord or the peripheral motor nerves.

In the context of the invention, the term "treatment" designates preventive, curative, palliative treatment, as well as caring for patients (reduction of suffering, improvement in life span, slowing down the progression of the disease), etc. The treatment can moreover be carried out in combination with other ingredients or treatments, such as in particular other active compounds for treating the pathologies or traumatisms specified in the present Application.

The subject components also have properties which inhibit the effect of positive allosteric modulators of the GABA$_A$ (gamma amino butyric acid of type A) receptors. Examples of positive allosteric modulators are: allopregnanolone or 3α-hydroxy-5α-pregnan-20-one or 3α,5α-TH-PROG or tetrahydrodeoxycorticosterone=3α,20-dihydroxy-5α-pregnan-20-one=3α,5α-TH-DOC, which are endogenous neurosteroids of the central nervous system. These specific properties justify that the compounds of the invention can also be of use in the treatment of different physiopathological situations where these neurosteroids have been described as playing an important role, such as for example, sexual behaviour
sudden death of the newborn, and in particular
painful sensitivity or chronic neuropathic pain
anxiety or depression
traumatic lesions of the nervous system
steroid-sensitive epilepsy, sleep disorders or alcohol intoxication
cognitive learning or memory disorders.

In particular, due to their neuroprotective properties vis à vis the motor neurons, they are of particular use in the treatment of amyotrophies, in particular amyotrophic lateral sclerosis or infantile spinal muscular atrophy, and in the treatment of traumas of the spinal cord or the peripheral motor nerves as mentioned above.

In general the daily dose of compound is the minimum dose to obtain the therapeutic effect. This dose will depend on the different factors mentioned previously. The doses of the compounds described above and for example cholest-4-en-3-one oxime are in general comprised between 0.001 to 100 mg per kilo per day for man.

If necessary, the daily dose can be administered in two, three, four, five, six or more, doses per day or by multiple sub-doses administered at appropriate intervals during the day.

The quantity chosen will depend on multiple factors, in particular the administration route, the duration of administration, the time of administration, the speed of elimination of the compound, the different product(s) used in combination with the compound, the age, weight and physical condition of the patient, as well as the patient's medical history, and all other information known in medicine.

The prescription of the attending physician can start at doses lower than those generally used, then these doses will be progressively increased in order to better control the appearance of possible side effects.

A subject of the invention is also the pharmaceutical compositions which contain at least one above-mentioned compound or one of its addition salts with pharmaceutically acceptable acids, as active ingredient.

In these compositions, the active ingredient is advantageously present at physiologically effective doses; the above-mentioned compositions contain, in particular, an effective neuroprotectrive dose of at least one of the above active ingredients.

As medicaments, the compounds corresponding to formula I as well as their addition salts with pharmaceutically acceptable acids can be incorporated in pharmaceutical compositions intended for the digestive or parenteral route.

The pharmaceutical compositions according to the invention can comprise moreover at least one other therapeutically active ingredient, for use which is simultaneous, separated or spread over time, in particular during a treatment for a subject suffering from a pathology or a trauma linked to the degeneration or to death of the motor neurons as defined above.

The pharmaceutical compositions or medicaments according to the invention advantageously include one or more inert excipients or vehicles, i.e. pharmaceutically inactive and non toxic. There can be mentioned for example saline, physiological, isotonic, buffered solutions, etc., compatible with pharmaceutical use and known to a person skilled in the art. The compositions can contain one or more agents or vehicles chosen from dispersants, solubilizing agents, stabilizers, preservatives, etc. Agents or vehicles which can be used in formulations (liquids and/or injectable solutions and/or solids) are in particular methylcellulose, hydroxymethylcellulose, carboxymethylcellulose, cyclodextrins, polysorbate 80, mannitol, gelatin, lactose, vegetable or animal oils, acacia, etc. The compositions can be formulated in the form of injectable suspensions, gels, oils, tablets, suppositories, powders, gelatin capsules, capsules, etc., optionally using galenic forms or devices ensuring a sustained and/or controlled release. For this type of formulation, an agent such as cellulose, carbonates or starches is advantageously used.

Administration can be carried out by any method known to a person skilled in the art, preferably by oral route or by injection, typically by intra-peritoneal, intra-cerebral, intra-thecal, intravenous, intra-arterial or intra-muscular route. Administration by oral route is preferred. If it is a question of a long term treatment, the preferred administration route is sublingual, oral or transcutaneous.

For injections, the compounds are generally packaged in the form of liquid suspensions, which can be injected using syringes or perfusions, for example.

It is understood that the flow rate and/or the dose injected or generally the dose to be administered, can be adapted by a person skilled in the art as a function of the patient, the pathology, administration method, etc. It is understood that the repeated administrations can be carried out, optionally in combination with other active ingredients or any vehicle which is acceptable on the pharmaceutical level (buffers, saline, isotonic solutions, in the presence of stabilizing agents, etc.).

The invention can be used in mammals, in particular in humans.

A subject of the present invention is also a process for the preparation of a composition described above, characterized in that the active ingredient or ingredients are mixed, according to the methods known per se, with acceptable excipients, in particular pharmaceutically acceptable.

The compounds of formula I as defined above are known or can be prepared according to the processes described in the literature. Certain derivatives of formula I are novel products.

This is why a subject of the present invention is also the novel compounds corresponding to formula I

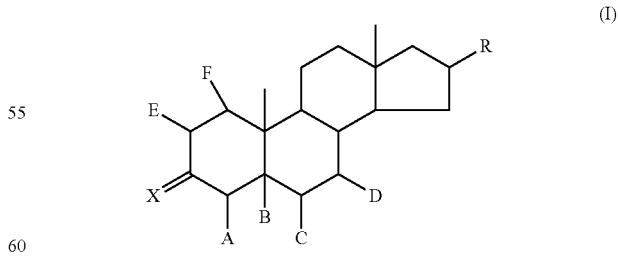

(I)

in which X represents an =NH—OH radical and
A represents together with B a carbon-carbon bond, C, D represent a hydrogen atom, E represents together with F a carbon-carbon bond and R has the meaning R1,
A represents together with B a carbon-carbon bond, C, D represent a hydrogen atom, E, F represent a hydrogen atom and R has the meaning R2 or R3 or R4, A represents together with B a carbon-carbon bond, C represents together with D a carbon-carbon bond, E, F represent a hydrogen atom and R has the meaning R6, A represents together with B a carbon-carbon bond, C represents together with D a carbon-carbon bond, E represents together with F a carbon-carbon bond and R has the meaning R1, as well as their addition salts with the mineral or organic acids.

A subject of the present invention is also a process for the preparation of novel compounds of formula I as defined above as well as their salts, characterized in that a compound of formula II

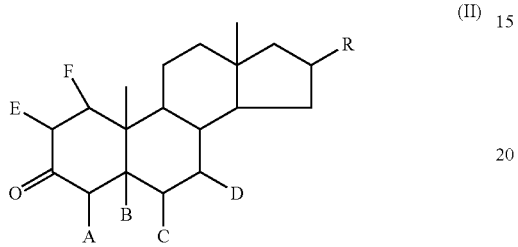

(II)

in which

A represents together with B a carbon-carbon bond, C, D represent a hydrogen atom, E represents together with F a carbon-carbon bond and R has the meaning R1, A represents together with B a carbon-carbon bond, C, D represent a hydrogen atom, E, F represent a hydrogen atom and R has the meaning R2 or R3 or R4, A represents together with B a carbon-carbon bond, C represents together with D a carbon-carbon bond, E, F represent a hydrogen atom and R has the meaning R6, A represents together with B a carbon-carbon bond, C represents together with D a carbon-carbon bond, E represents together with F a carbon-carbon bond and R has the meaning R1, is reacted with a hydroxylamine halide such as hydroxylamine hydrochloride, in order to obtain the expected compound of formula I which is isolated and if desired salified.

Under preferential conditions for implementing the process described above, the starting product is solubilized in a minimum amount of a suitable solvent such as pyridine if another ketone function is present, it is specifically blocked by a suitable protective group such as cyclic acetals, an excess, for example 2 equivalents, of hydroxylamine halide is used.

the operation is carried out under stirring for approximately 24 hours at ambient temperature.

The compounds of formula II are known derivatives, described in the literature, and are commercially accessible.

A subject of the invention is also the use of a compound of formula I

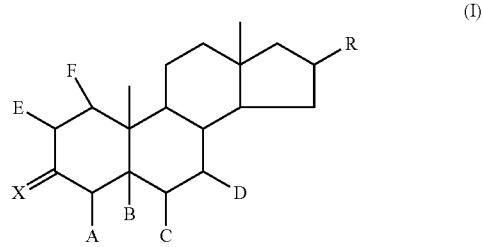

(I)

in which X represents an oxygen atom or an =N—OH group,

R represents a group chosen from

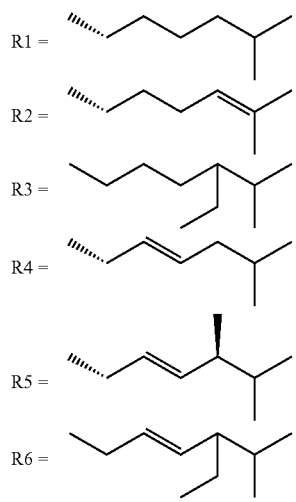

A represents a hydrogen atom or together with B a carbon-carbon bond

B represents a hydrogen atom, a hydroxy group or together with A a carbon-carbon bond, C represents a hydrogen atom or together with D a carbon-carbon bond, D represents a hydrogen atom or together with C a carbon-carbon bond, E represents a hydrogen atom or together with F a carbon-carbon bond, F represents a hydrogen atom or together with E a carbon-carbon bond, as well as cholest-4,24-dien-3-one, 24-methylcholest-4,6,22-trien-3-one, or cholest-5-en-3-one oxime or one of its addition salts with pharmaceutically acceptable acids, for obtaining a neuroprotective medicament, in particular intended for the treatment of neurodegenerative diseases such as for example Huntington's disease, hereditary or sporadic, chronic neurodegenerative diseases, neuronal lesions linked with ageing, hereditary peripheral neuropathies or peripheral neuropathies resulting from a lesion, Charcot-Marie-Tooth disease, diabetic neuropathies or neuropathies induced by anti-cancer treatments, traumas of the brain, of the peripheral nerves or of the spinal cord, ischemias of the brain or the spinal cord, degenerations which are hereditary, resulting from a lesion or linked with ageing of the sensory neurons of vision or degenerations of the optic nerve, degenerations which are hereditary, traumatic or linked with ageing of the sensory neurons of hearing, lobar atrophies and vascular dementias, the diseases and traumas linked to the degeneration of motor neurons and more particularly the spinal amyotrophies particularly infantile, amyotrophic lateral sclerosis, multiple sclerosis and the traumas of the spinal cord or the peripheral motor nerves.

A particular subject of the invention is the use of a compound of formula I above for obtaining a neuroprotective medicament, in particular intended for the treatment of pathologies or traumas linked to the degeneration or death of the neurons, in mammals (in general patients) suffering from such pathologies or traumatisms.

A more particular subject of the invention is the use of a compound of formula I for obtaining a medicament intended for the treatment of infantile spinal muscular atrophy and amyotrophic lateral sclerosis.

A subject of the invention is also the use of a compound of formula I above for obtaining a medicament intended for the treatment of the pathologies where the overactivation of the $GABA_A$ receptors, (for example as a result of the presence of neurosteroids such as allopregnanolone and/or tetrahydrodeoxycorticosterone), can have a harmful effect such as steroid-sensitive epilepsies, alcohol intoxication, cognitive learning, painful sensitivity or sleep disorders. This overactivation of the $GABA_A$ receptors, can be characterized by the inhibitory effects or the stimulating effects.

The use of these medicaments usually comprises the administration to these mammals of a therapeutically effective quantity of a compound of formula I and in particular cholest-4-en-3-one oxime, in particular for increasing the survival of the neurons or encouraging axonal growth.

The invention just as much relates to a treatment method for diseases, in particular neurodegenerative, mentioned above and in particular a treatment method for pathologies or traumas linked to the degeneration or death of the neurons, in mammals (in general patients) suffering from such pathologies or traumas, comprising the administration to these mammals of a therapeutically effective quantity of cholest-4-en-3-one oxime, in particular for increasing the survival of the neurons or encouraging axonal growth.

In addition a subject of the invention is a treatment method for one of the diseases described above and in particular the pathologies or traumas linked to the degeneration or death of the motor neurons, in mammals (in general patients) suffering from such pathologies or traumas, comprising the administration to these mammals of a therapeutically effective quantity of a compound of formula I, in particular for increasing the survival of the neurones. More specifically, the pathologies linked to the degeneration or death of the motor neurons are amyotrophic lateral sclerosis or infantile spinal amyotrophies.

The invention relates both to the provision of novel derivatives of 4-cholesten-3-one and to derivatives of 4-cholesten-3-one other than those which may have been described in the state of the art. Those described in the literature are therefore excluded.

The preferential conditions described above for the use of the medicaments of formula I also apply to the other subjects of the invention mentioned above, in particular to compositions, novel derivatives, uses and treatment methods and vice versa.

The examples which follow illustrate the present application.

EXAMPLE 1

A suspension was prepared corresponding to the formula

| Cholest-4-en-3-one oxime | 20 mg per ml |
|---|---|
| Excipient: | Oily emulsion |

EXAMPLE 2

Soft gelatin capsules were prepared corresponding to the formula

| Cholest-4-en-3-one oxime | 250 mg |
|---|---|
| Excipient: | |
| sufficient quantity for a gelatin capsule completed at | 750 mg |

EXAMPLE 3

1,4-cholestadien-3-one oxime (R=R1)

5 g of 1,4-cholestadien-3-one (13 mmol) is solubilized in 50 ml of pyridine in a 100 ml flask, then 5 g of hydroxylamine hydrochloride is added. Stirring is maintained for 24 hours at ambient temperature, and the solvent is evaporated off under reduced pressure. Water then ethyl acetate are added in order to carry out an extraction. The organic phase is washed with an acidified aqueous solution (HCl 1%). The ethyl acetate is evaporated off under reduced pressure. A white powder is obtained with a yield greater than 50%.

Analysis

Liquid chromatography/Mass spectrometry (Electrospray®)

Conditions of the high-performance liquid chromatography:

Column: Macherey-Nagel—Nucleosil® 300-6 C4—150× 4.6 mm

Gradient: water (+0.05% TFA)/acetonitrile (+0.05% trifluoroacetic acid)

t=0 min: 60% acetonitrile, 40% $H_2O$ t=6 min: 100% acetonitrile, 0% $H_2O$

Then 100% acetonitrile for 5 min.

Retention time: 5 min 60 seconds

Peak detected by mass spectrometry: $\{M+H\}^+=398$

EXAMPLE 4

4,24-cholestadien-3-one oxime (R=R 2)

100 mg of 4,24-cholestadien-3-one (0.26 mmol) is solubilized in 5 ml of pyridine in a 10 ml flask, then 100 mg of hydroxylamine hydrochloride is added. Stirring is maintained for 24 hours at ambient temperature, and the solvent is evaporated off under reduced pressure. Water then ethyl acetate are added in order to carry out an extraction. Then the organic phase is washed with an acidified aqueous solution (HCl 1%). The ethyl acetate is evaporated off under reduced pressure. A white powder is obtained with a yield greater than 50%.

Analysis

Liquid chromatography/Mass spectrometry (Electrospray®)

Peak detected by mass spectrometry: $\{M+H\}^+=398$

EXAMPLE 5

4,22-cholestadien-3-one oxime (R=R 4)

10 mg of 4,22-cholestadien-3-one (0.026 mmol) is solubilized in 5 ml of pyridine in a 10 ml flask, then 100 mg of hydroxylamine hydrochloride is added. Stirring is maintained for 24 hours at ambient temperature, and the solvent is evaporated off under reduced pressure. Water then ethyl acetate are added in order to carry out an extraction. Then the organic phase is washed with an acidified aqueous solution (HCl 1%). The ethyl acetate is evaporated off under reduced pressure. A white powder is obtained with a yield greater than 50%.

Analysis

Liquid chromatography/Mass spectrometry (Electrospray®)

Peak detected by mass spectrometry: $\{M+H\}^+=398$

EXAMPLE 6

4-stigmasta-ene-3-one oxime (R=R 3)

100 mg of 4-stigmasta-ene-3-one (0.24 mmol) is solubilized in 10 ml of pyridine in a 50 ml flask, then 100 mg of hydroxylamine hydrochloride is added. Stirring is maintained for 24 hours at ambient temperature, and the solvent is evaporated off under reduced pressure. Water then ethyl acetate is added in order to carry out an extraction. Then the organic phase is washed with an acidified aqueous solution (HCl 1%). The ethyl acetate is evaporated off under reduced pressure. A white powder is obtained with a yield greater than 50%.

Analysis
Liquid chromatography/Mass spectrometry (Electrospray®)
Peak detected by mass spectrometry: ${M+H}^+=428$

EXAMPLE 7

4.6, 22-ergosta-trien-3-one oxime (R=R 6)

100 mg of 4,6,22-ergosta-trien-3-one (0.25 mmol) is solubilized in 10 ml of pyridine in a 50 ml flask, then 100 mg of hydroxylamine hydrochloride is added. Stirring is maintained for 24 hours at ambient temperature, and the solvent is evaporated off under reduced pressure. Water then ethyl acetate are added in order to carry out an extraction. Then the organic phase is washed with an acidified aqueous solution (HCl 1%). The ethyl acetate is evaporated off under reduced pressure. A white powder is obtained with a yield greater than 50%.

Analysis
Liquid chromatography/Mass spectrometry (Electrospray®)
Peak detected by mass spectrometry: ${M+H}^+=410$

EXAMPLE 8

1.4, 6-cholesta-trien-3-one oxime (R=R1)

100 mg of 1,4,6-cholesta-trien-3-one (0.26 mmol) is solubilized in 10 ml of pyridine in a 50 ml flask, then 100 mg of hydroxylamine hydrochloride is added. Stirring is maintained for 24 hours at ambient temperature, and the solvent is evaporated off under reduced pressure. Water then ethyl acetate are added in order to carry out an extraction, then the organic phase is washed with an acidified aqueous solution (HCl 1%). The ethyl acetate is evaporated off under reduced pressure. A white powder is obtained with a yield greater than 50%.

Analysis
Liquid chromatography/Mass Spectrometry (Electrospray®)
Peak detected by mass spectrometry: ${M+H}^+=396$ Pharmacological Study
The following compounds of formula I were tested:

| No. | |
|---|---|
| 1 | Cholest-4-en-3-one oxime described in Gamma irradiation of cholestenone oximes. Uenseren, Envare. Cekmece Nucl. Res. Train. Cent., Istanbul, Turk. Avail. INIS. Report (1976), (CNAEM-R-157), 21 pp. From: INIS Atomindex 1977, 8(6), Abstr. No. 295540. |
| 2 | Compound of Example 3 |
| 3 | Cholestan-3-one oxime commercially available from Sigma-Aldrich |
| 4 | Cholest-4,24-dien-3-one described in Chemical synthesis of cholest-5,7,24-trien-3beta-ol and demonstration of its conversion to cholesterol in the rat. Scallen, Terence J. Univ. of Minnesota, Minneapolis, Biochemical and Biophysical Research Communications (1965), 21(2), 149-55. |
| 5 | 4,22-cholest-dien-3-one described in 3-Keto-Δ4-steroids from 3-hydroxy-ene-4 (or ene-5)-steroids. Yamanaka, Toru; Imai, Takashi. (Takasago Perfumery Co., Ltd., Japan). JP 52116456 19770929 Showa. Application: JP 76-32979 19760325. CAN 88: 136852 AN 1978: 136852 |
| 6 | Compound of Example 4 |
| 7 | Compound of Example 5 |
| 8 | Compound of Example 6 |
| 9 | 5-beta-hydroxy-cholestan-3-one commercially available from Sigma-Aldrich |
| 10 | 5-alpha-hydroxy-cholestan-3-one commercially available from Sigma-Aldrich |
| 11 | 5-alpha-cholest-6-en-3-one commercially available from Sigma-Aldrich |
| 12 | 24-methylcholest-4,6,22-trien-3-one described in Preparation of 3-beta-hydroxy-(24R)-methylcholest-5-ene. Khripach, V. A.; Zhabinskii, V. N.; Zhernosek, E. V.; Lakhvich, F. A. (Institute of Bioorganic Chemistry, Academy of Sciences, Belorussian S.S.R., USSR). U.S.S.R. (1990), and SU 1594181 19900923: SU 88-4612746 19881201. CAN 114: 102558 AN 1991: 102558 |
| 13 | Cholest-5-en-3-one oxime-described in Gamma irradiation of cholestenone oximes. Uenseren, Envare. Cekmece Nucl. Res. Train. Cent., Istanbul, Turk. Avail. INIS. Report (1976), (CNAEM-R-157), 21 pp. |
| 14 | Cholest-4,6-dien-3-one oxime described in Azasteroid from cholesta-4,6-dien-3-one. Ahmad, Mohammed S.; Siddiqui, A. H.; Shafiullah; Logani, S. C. Aligarh Muslim Univ., Aligarh, India. Australian Journal of Chemistry (1969), 22(1), 271-4. |
| 15 | Compound of Example 7 |
| 16 | 5-alpha-cholest-1-en-3-one oxime described in Polyphosphoric acid-catalyzed Beckmann rearrangement of 3-keto-steroid oximes. Kobayashi, Masaru; Shimizu, Yuzuru; Mitsuhashi, Hiroshi. Fac. Pharm. Sci., Hokkaido Univ., Sapporo, Japan. Chemical & Pharmaceutical Bulletin (1969), 17(6), 1255-60. |
| 17 | Compound of Example 8 |

1. Effects of the Compounds of Formula I on the Survival of the Motor Neurons

In order to demonstrate the neuroprotective action of the compounds of formula I, the applicant studied their activity on an in vitro model of trophic deprivation of rat motor neurons. Reference can advantageously be made to the applicant's patent application WO 0142784 on the culturing of motor neurons of the spinal cord.

The spinal cord of E14 rat embryos is dissected and the ventral part is isolated by trituration after trypsination. The motor neurons are separated from the other spinal cells by a known method (Camu et al., 1993, Purification of spinal motor neurons from chicken and rat embryos by immunopanning. In <<Immunoselection Strategies for Neural cell culture>>, Neuroprotocols: A companion to Methods in Neurosciences 2, 191-199; Henderson et al., 1993, Neutrophins promote motor neuron survival and are present in embryonic limb bud. Nature 363 (6426):266-70). The cells are centrifuged on a density gradient. The motor neurons are enriched in the fraction of the large cells (the least dense). The cells of this fraction are incubated with an anti-p75 antibody, a surface antigen present on the motor neurons. Secondary antibodies coupled with magnetic balls are added and the mixture of cells is passed through a column in a magnet (Arce et al., 1999). Only the motor neurons are retained: their purity is of the order of 90%.

The motor neurons are inoculated at low density in culture wells on a substrate of polyornithine-laminin in a neurobasal medium supplemented according to Raoul et al., 1999, Programmed cell death of embryonic motor neurons triggered through the Fas death receptor. J Cell Biol 147(5):1049-62. Negative controls (absence of trophic factors) and positive controls (in the presence of BDNF (Brain-Derived Neurotrophic Factor) at 1 ng/ml, GDNF (Glial-Derived Neurotrophic Factor) at 1 ng/ml and CNTF (Ciliary Neurotrophic Factor) at 10 ng/ml, marketed by the American company PEPROTECH, Inc. and the Sigma-Aldrich company, are included in each series.

The compounds to be tested are added 60 minutes after the inoculation and the cultures are maintained at 37° C. under 5% $CO_2$ for 3 days.

The motor neurons have a spontaneous tendency to die in the absence of neurotrophic factors (Pettmann and Henderson, 1998, Neuronal cell death. Neuron 20 (4):633-47). After 3 days, the survival is evaluated by a fluorescence measurement after incubation of the cells in the presence of calcein which becomes fluorescent in the living cells.

After 3 days in culture at 37° C., under 5% $CO_2$ and in saturating humidity, up to 50% of the motor neurons initially inoculated survive in the medium supplemented with neurotrophic factors, while less than 15% of the motor neurons survive in basal medium alone.

The activity of the compounds to be tested was evaluated according to their capacity to prevent the death of the motor neurons when they are added to the neurobasal medium compared with the survival of the motor neurons in medium supplemented with neurotrophic factors.

The compounds of formula I according to the invention have shown an activity with a concentration capable of allowing a better survival rate of the motor neurons in the basal medium. This survival rate is expressed by a number, the ratio. If the ratio is greater than 0, the effect of the compounds on the survival of the motor neurons is positive.

The results obtained are as follows:

| Compound No. | Concentration in μM | Ratio |
| --- | --- | --- |
| 1 | 5 | 1 |
| 2 | 5 | 0.6 |
| 6 | 5 | 0.5 |
| 7 | 6 | 0.25 |
| 8 | 10 | 0.3 |
| 15 | 5 | 0.2 |
| 17 | 5 | 0.3 |
| 9 | 1 | 0.5 |

Because of their trophic effect on the spinal motor neurons, the compounds of formula I according to the invention therefore prove to be useful as a medicament, in particular in the treatment of amyotrophies, in particular in the treatment of amyotrophic lateral sclerosis or infantile spinal muscular atrophy, and in the treatment of traumas of the spinal cord.

2. Effects of the Compounds of Formula I on Neuroprotection

An axotomy of the facial nerve is performed on new-born young rats of 2-3 days old. The animals receive the cholest-4-en-3-one oxime 4 hours before the unilateral section of the nerve then daily for 5 days by sub-cutaneous route. Seven days after the section of the nerve, the animals are anaesthetized, then fixed by intra-cardial perfusion of paraformaldehyde. The brain is then removed and placed in paraffin. The histological analysis of compound sections of 7 μm of the nucleus of the facial nerve, stained with cresyl violet, allows the number of motor neurons of the intact side as well as of the side of the nerve which has been sectioned to be counted (Casanovas et al., Prevention by lamotrigine, MK-801 and N omega-nitro-L-arginine methyl ester of motoneuron cell death after neonatal axotomy, Neuroscience, 1996, 71, 313-325).

The results obtained are as follows:

The survival of the motor neurons of the nucleus of the facial nerve in new-born rats which are axotomized and treated with cholest-4-en-3-one oxime is increased up to 40% at a dose comprised between 3 and 100 mg/kg, according to the administration route, compared with the nerve which is not sectioned.

3. Effects of the Compounds of Formula I on Neuroprotection

Crushing of the sciatic nerve is carried out on adult mice according to the method described by Azzouz et al., Enhancement of mouse sciatic nerve regeneration by the long chain fatty alcohol, N-hexacosanol, Exp. Neurol., 1996, 138: 189-97). The animals receive the compounds to be tested the day of the crushing then each day for 4 weeks and by sub-cutaneous route. Each week the animals are anaesthetized in order to make an electromyographic recording in the calf muscle after supramaximal stimulation of the sciatic nerve. The amplitude, the duration and the latency of the action potentials mentioned (CMAP) are thus measured. Four weeks after the crushing of the nerve, the animals are sacrificed by injection of a lethal dose of anaesthetic and a segment of damaged nerve is sampled, fixed in 4% glutaraldehyde and placed in resin. The histological analysis of compound sections, stained with toluidine blue, allows a semi-automated counting of the degenerated and non-degenerated fibres, as well as a measurement of the size of the axons and of the thickness of the myelin sheath of the non-degenerated fibres.

The results obtained are as follows:

The administration of cholest-4-en-3-one oxime reduces from 20 to 40% the number of degenerated fibres compared with the non-treated animals. In a still more spectacular way, the regeneration of the nerve fibres is greatly stimulated by the compounds to be tested from the second week after the crushing, with a maximum effect observed four weeks after the crushing. Thus four weeks after the crushing, the amplitude of the CMAPs in the mice treated with the compounds to be tested at a dose between 0.3 and 30 mg/kg/day, according to the administration route, is increased by 40 to 70% and the nerve conduction velocity is improved by 30 to 50% compared with the non-treated mice.

4. Effects of the Compounds of Formula I on Protection of Striatal Neurons from Death Induced by the Overexpression of a Mutated Form of Huntingtin Primary cultures of striatal neurons are prepared as described in the literature (Primary striatal neuronal culture, Mao L. et al., Methods Mol. Med., 2003, 79:379-86). The cells undergo electroporation according to the procedure described by Raoul et al., (Motoneuron death triggered by a specific pathway downstream of Fas. potentiation by ALS-linked SOD1 mutations Neuron, 2002, 35:1067-83) before inoculation with an expression vector or plasmid containing a promoter element followed by the DNA coding for a truncated form of huntingtin which comprises the first 480 amino acids and 68 CAG (Saudou et al., huntingtin acts in the nucleus to induce apoptosis but death does not correlate with the formation of intranuclear inclusions, Cell, 1998, 95:55-66). A second expression vector containing the DNA coding the green fluorescent protein (GFP) also undergoes electroporation and serves as a reporter gene. The DNA of the plasmid coding the huntingtin was prepared by purification with cesium chloride. The plasmid containing the GFP sequence was prepared on Qiagen columns. The integrity of the DNA sequences is verified by sequencing, transfection and western blotting. The cells which survive the electroporation are inoculated at a density of 4000 cells per well of a 96-well plate. The culture takes place in Neurobasal medium (GIBCO) complimented with pyruvate and B-27 (Beckton Dickinson). The cells are maintained in culture for 7 days without changing the medium.

The treatments with the compounds to be tested are carried out just after the inoculation at a final concentration of 1 µM in 0.5% of dimethyl sulphoxide (DMSO). The positive controls are carried out by the addition of BDNF at 5 ng/ml final. The negative controls only receive 0.5% DMSO.

Cell death is evaluated after the 7 days by counting the number of living cells expressing the GFP.

The activity of the compounds to be tested was evaluated by their capacity to prevent the death of the striatal neurons cultured in the neurobasal medium compared with the survival of the striatal neurons in medium supplemented with BDNF (Brain-Derived Neurotrophic Factor).

The results obtained are as follows:

| Compound No. | Concentrations in µM | Ratio |
|---|---|---|
| 1 | 1 | 0.3 |
| 4 | 1 | 0.2 |
| 9 | 1 | 0.5 |
| 11 | 1 | 0.3 |
| 12 | 1 | 0.3 |

At the concentration of $10^{-6}$ M, the compounds to be tested demonstrate an protective effect against cell death induced by mutated huntingtin of up to 60 compared with the cells treated with BDNF.

Because of their neuroprotective effect, the compounds of formula I according to the invention thus prove to be useful as medicaments intended for the treatment or the prevention of neurodegenerative diseases, in particular in the treatment of spinal amyotrophies, amyotrophic lateral sclerosis, in the treatment of traumatisms of the spinal cord and of the peripheral nerves and in the treatment of Huntington's chorea.

5. Effects of the Compounds of Formula I on the Potentialization of the $GABA_A$ Receptors by Steroids Electrophysiological experiments were carried out in vitro with rat neurons (slices of hippocampus, neurons sensitive in culture), as follows:

The experiments are carried out with hippocampi removed from rats of the Sprague Dawley strain aged from 10 to 21 days. The animals are sacrificed by decapitation, and their brain is rapidly transferred into ACSF (Artificial Cerebro-Spinal Fluid) without sodium (composition: 2 mM KCl, 1.2 mM $NaH_2PO_4$, 2 mM $MgCl_2$, 0.5 mM $CaCl_2$, 26 mM $NaHCO_3$, 11 mM glucose, 250 mM saccharose), maintained at a temperature of 4° C. and carbogen (a 95% $O_2$, 5% $CO_2$ mixture) is bubbled through. The hippocampi are extracted from each cerebral hemisphere then cut up into slices of 300 µM thickness using a "tissue chopper". The slices are left to rest in ACSF medium (composition: 126 mM NaCl, 2 mM KCl, 1.2 mM $NaH_2PO_4$, 2 mM $MgCl_2$, 0.5 mM $CaCl_2$, 26 mM $NaHCO_3$, 11 mM glucose) at ambient temperature, at least one hour before recording. Using a pipette, one slice is then deposited on a multi-electrode recording system (MEA, MultiChannel Systems™, Germany) and positioned so as to cover the 64 electrodes. In order to avoid any change in position by the perfusion flow, a grid weighted down by a platinum <<U>> is positioned on the slice. The MEA is then rapidly inserted into the recording system and the chamber perfused with ACSF with carbogen bubbled through; the middle of the chamber is connected to earth. The perfused ACSF as well as the MEA are maintained at a temperature of 37° C. One of the 60 electrodes is selected as a stimulation electrode. A biphasic stimulation current with an intensity of 300 µA over 0.1 ms is generated from this electrode at a rate of one stimulation every 30 seconds. The responses produced are seen simultaneously at the level of the 59 other electrodes of the MEA. The axons of the Schaeffer collaterals are stimulated in the CA3. In the CA1 region, 6 to 12 electrodes are selected in order to record the field potentials which correspond to the sum of the variations of the postsynaptic potentials of the neurons situated close to each electrode. The molecules tested are dissolved in the ACSF medium (the final concentration of DMSO is $\leq 0.1\%$) and carried over onto the slice by means of the perfusion system.

The sensitive rat neurons are cultured for 1 to 2 days and then recorded with the patch clamp technique as described in De Roo M. et al. (Dehydroepiandrosterone potentiates native ionotropic ATP receptors containing the P2X2 subunit in rat sensory neurones, J Physiol, 2003, 552:59-71).

The results obtained are as follows:

On the slices of hippocampus, a small fraction of the postsynaptic field potentials recorded in the CA1 region corresponds to a stimulating $GABA_A$ transmission: it is blocked by standard antagonists of the $GABA_A$ receptors (20 µM bicuculline or 50 µM picrotoxin) and potentialized by positive allosteric modulators of the $GABA_A$ receptors: benzodiazepine (1-10 µM of diazepam) and steroids (10-1000 nM allopregnanolone or tetrahydrodeoxycorticosterone). The potentializing effect of the steroids disappears when the $GABA_A$ receptors are desensitized by the addition of a saturating concentration of GABA (10 mM). The stimulating effect of the GABA is linked to the passage of the bicarbonate ions (HCO$_3^-$) through the GABA$_A$ receptors.

In the sensitive neurons recorded with patch-clamp, currents are produced by selectively opening the GABA$_A$ receptors of these neurons by rapidly applying a GABA$_A$-selective agonist, isoguvacine. The chlorine currents thus produced are blocked by bucuculline and potentialized by allopregnanolone.

The results show that cholest-4-en-3-one oxime (tested alone up to 10 µM) has no effect on the GABA$_A$ receptors (slice of hippocampus or sensitive neurons). By contrast, cholest-4-en-3-one oxime is capable of blocking the effect of positive allosteric modulators (allopregnanolone or tetrahydrodeoxycorticosterone) of the GABA$_A$ receptors in a dose-dependent way and for concentrations equivalent to those where neurotrophic effects are observed in vitro.

The compounds of formula I therefore have a "protective" effect in all the pathologies where the overactivation of the GABA$_A$ receptors, due to the presence of allopregnanolone and/or tetrahydrodeoxycorticosterone, can have a harmful effect, either for inhibitory effects or on stimulating effects mediated by the GABA$_A$ receptors.

Toxicological Study

The administration to mice, in particular of cholest-4-en-3-one oxime, by oral, sub-cutaneous, intra-peritoneal and intravenous routes, at doses ranging up to 300 mg/kg/day per treatment with a daily administration which can last up to 28 days, did not show significant toxicity.

In monkeys, the administration by oral route of increasing daily doses up to 1500 mg/kg over a period of 10 days revealed no toxicity.

The invention claimed is:

1. A method for providing neuroprotection to a patient suffering from spinal muscular atrophy (SMA), comprising administering to the patient a neuroprotective-effective amount of a compound of formula I

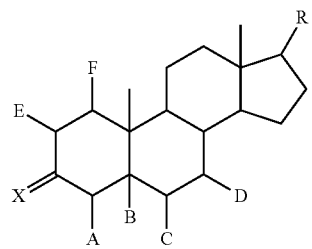

in which X is an oxygen atom or an =N—OH group,

R is selected from the group consisting of

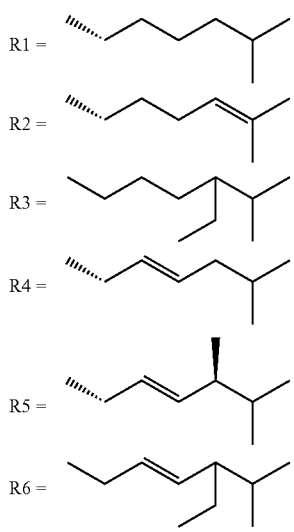

A is a hydrogen atom or together with B a carbon-carbon bond,

B is a hydrogen atom, a hydroxy group or together with A a carbon-carbon bond,

C is a hydrogen atom or together with D a carbon-carbon bond,

D is a hydrogen atom or together with C a carbon-carbon bond,

E is a hydrogen atom or together with F a carbon-carbon bond,

F is a hydrogen atom or together with E a carbon-carbon bond, or an addition salt with a pharmaceutically acceptable acid.

2. The method of claim 1, wherein the compound of formula I is cholest-4-en-3-one oxime.